(12) United States Patent
Zehavi et al.

(10) Patent No.: US 12,396,805 B2
(45) Date of Patent: Aug. 26, 2025

(54) SYSTEMS, METHODS, AND DEVICES FOR DRILLING AND IMAGING AN ANATOMICAL ELEMENT

(71) Applicant: Mazor Robotics Ltd., Caesarea (IL)

(72) Inventors: Eliyahu Zehavi, Tel Aviv (IL); Yonatan Ushpizin, Glil Yam (IL)

(73) Assignee: Mazor Robotics Ltd., Caesarea (IL)

( * ) Notice: Subject to any disclaimer, the term of this patent is extended or adjusted under 35 U.S.C. 154(b) by 760 days.

(21) Appl. No.: 17/590,915

(22) Filed: Feb. 2, 2022

(65) Prior Publication Data

US 2023/0240763 A1 Aug. 3, 2023

(51) Int. Cl.
| | |
|---|---|
| *A61B 34/00* | (2016.01) |
| *A61B 17/00* | (2006.01) |
| *A61B 17/16* | (2006.01) |
| *A61B 17/17* | (2006.01) |
| *A61B 34/30* | (2016.01) |
| *A61B 90/00* | (2016.01) |

(52) U.S. Cl.
CPC .......... *A61B 34/25* (2016.02); *A61B 17/1615* (2013.01); *A61B 17/1703* (2013.01); *A61B 34/30* (2016.02); *A61B 90/03* (2016.02); *A61B 90/37* (2016.02); *A61B 2017/00115* (2013.01); *A61B 2034/252* (2016.02); *A61B 2090/033* (2016.02); *A61B 2090/3784* (2016.02); *A61B 2217/005* (2013.01); *A61B 2217/007* (2013.01)

(58) Field of Classification Search
CPC ......... A61B 34/25; A61B 34/30; A61B 90/03; A61B 90/37; A61B 17/1615; A61B 17/1703
See application file for complete search history.

(56) References Cited

U.S. PATENT DOCUMENTS

| | | | |
|---|---|---|---|
| 6,719,692 B2 | 4/2004 | Kleffner et al. | |
| 7,748,273 B2 | 7/2010 | Halevy-Politch et al. | |
| 2017/0333052 A1* | 11/2017 | Ding | A61B 17/00234 |
| 2019/0041195 A1* | 2/2019 | El Zoghbi | A61B 90/03 |
| 2021/0378689 A1* | 12/2021 | Tyndall | A61B 34/10 |

FOREIGN PATENT DOCUMENTS

| | | | |
|---|---|---|---|
| DE | 102011111671 | 2/2013 | |
| KR | 10-1795928 | 11/2017 | |
| WO | WO 2019/134942 | 7/2019 | |
| WO | WO-2019134942 A1 * | 7/2019 | ......... A61B 17/1615 |
| WO | WO 2021/062373 | 4/2021 | |
| WO | WO-2021062373 A2 * | 4/2021 | ......... A61B 17/1615 |

OTHER PUBLICATIONS

International Search Report and Written Opinion for International (PCT) Patent Application No. PCT/IL2023/050087, dated Jul. 3, 2023, 19 pages.

* cited by examiner

*Primary Examiner* — Kevin T Truong
*Assistant Examiner* — Diana Jones
(74) *Attorney, Agent, or Firm* — Sheridan Ross P.C.

(57) ABSTRACT

Systems, methods, and devices for drilling and imaging an anatomical element are provided. An image may be received from an imaging device coupled to a housing. The image may depict hard tissue and/or soft tissue and the image may be processed using image processing to identify the hard tissue and/or soft tissue. A thickness of the hard tissue may be determined and instructions to perform a surgical step on the hard tissue when the thickness is less than a predetermined threshold may be transmitted.

19 Claims, 11 Drawing Sheets

SYSTEMS, METHODS, AND DEVICES FOR DRILLING AND IMAGING AN ANATOMICAL ELEMENT

BACKGROUND

The present disclosure is generally directed to tissue removal and imaging, and relates more particularly to drilling or milling an anatomical element and imaging the anatomical element.

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following removal of soft or hard tissue in the patient anatomy.

BRIEF SUMMARY

Example aspects of the present disclosure include:

A device for drilling and imaging an anatomical element according to at least one embodiment of the present disclosure comprises a processor; and a memory storing data for processing by the processor, the data, when processed, causes the processor to: receive an image from an imaging device coupled to a housing having a bore and a surgical tool disposed in the bore, the image depicting hard tissue; process the image using image processing to identify the hard tissue; determine a thickness of the hard tissue; and transmit instructions to perform a surgical step on the hard tissue when the thickness is less than a predetermined threshold.

Any of the aspects herein, wherein the imaging device is disposed at an end of the housing and surrounds the bore.

Any of the aspects herein, wherein the imaging device is disposed in the bore and adjacent to the surgical tool.

Any of the aspects herein, the memory stores further data for processing by the processor that, when processed, causes the processor to: extend at least one of the surgical tool or the imaging device from the housing.

Any of the aspects herein, wherein the surgical tool comprises a drill bit and the surgical step comprises drilling an anatomical element.

Any of the aspects herein, wherein the memory stores further data for processing by the processor that, when processed, causes the processor to: generate a notification when the thickness of the hard tissue meets a target thickness.

Any of the aspects herein, wherein the memory stores further data for processing by the processor that, when processed, causes the processor to: prevent the surgical tool from further advancement when the thickness of the hard tissue meets a target thickness.

Any of the aspects herein, wherein the imaging device comprises an ultrasound device.

A system for drilling and imaging an anatomical element according to at least one embodiment of the present disclosure comprises a housing comprising a bore; a surgical tool disposed in the bore, the surgical tool operable to extend from the bore and perform a surgical step; an imaging device disposed in the bore and adjacent to the drill bit, the imaging device operable to extend from the bore and obtain an image; a processor; and a memory storing data for processing by the processor, the data, when processed, causes the processor to: transmit instructions to perform the surgical step using the surgical tool; receive an image from the imaging device depicting hard tissue; process the image using image processing to identify the hard tissue; and determine a thickness of the hard tissue.

Any of the aspects herein, wherein the memory stores further data for processing by the processor that, when processed, causes the processor to: generate a notification when the thickness of the hard tissue meets or exceeds a thickness threshold.

Any of the aspects herein, wherein the surgical tool comprises a drill bit and the surgical step comprises drilling an anatomical element.

Any of the aspects herein, wherein the system further comprises: an irrigation source operable to provide liquid to the bore; and a vacuum source operable to remove the liquid from the bore.

Any of the aspects herein, wherein when the thickness of the hard tissue is less than a thickness threshold, the memory stores further data for processing by the processor that, when processed, causes the processor to: extend the surgical tool from the bore; transmit instructions to perform a surgical step using the surgical tool; and retract the surgical tool into the bore.

A system for milling and imaging an anatomical element according to at least one embodiment of the present disclosure comprises a housing having a bore and an extension extending from the housing; a surgical tool disposed in the bore, the surgical tool operable to extend from the bore and perform a surgical step; and an imaging device disposed at an end of the extension and opposite the surgical tool.

Any of the aspects herein, wherein the soft tissue and the hard tissue is positioned between the surgical tool and the imaging device.

Any of the aspects herein, wherein the memory stores further data for processing by the processor that, when processed, causes the processor to: generate a notification when the soft tissue does not separate from the hard tissue.

Any of the aspects herein, further comprising: at least one processor; and a memory storing data for processing by the processor, the data, when processed, causing the processor to: transmit instructions to perform the surgical step using the surgical tool; receive an image from the imaging device depicting hard tissue and soft tissue; process the image using image processing to identify the hard tissue and the soft tissue; and determine when the soft tissue has separated from the hard tissue.

Any of the aspects herein, wherein the surgical tool comprises a drill bit and the surgical step comprises milling an anatomical element.

Any of the aspects herein, wherein the extension comprises a first member extending from the housing and a second member extending from and perpendicular to the first member.

Any of the aspects herein, wherein the imaging device is at least one of attached to or integrated with the second member.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1A:
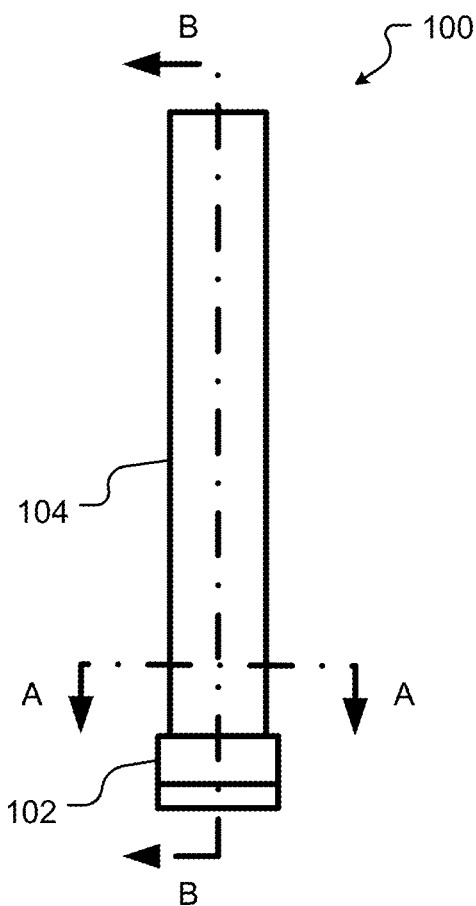
FIG. 1A is a front view of a system for drilling and imaging according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia Geforce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

With the use of medical robots in an operating room, a need for increased safety layers during use of the robots is desired. During an operation, the robot may be moving inside of a patient anatomy, such as, for example, through a port in soft tissue, in order to reach an internal anatomical element such as a bone. The robot may be used to drill or mill the bone. During such procedures, it is desirable to know in real-time, a location of a tool such as, for example, a drill bit, and in particular, a tip of the drill bit. Conventional methods for increasing safety during drilling or milling a bone do not support a closed loop solution providing real-time data.

At least one embodiment of the present disclosure provides for a system capable of detecting a minimum thickness of a bone being drilled to, for example, a remaining millimeter of drilling prior to touching sensitive soft tissue such as, for example, a spinal cord. Such system enables the avoidance of spinal cord tear due to adhesion barrier during spine surgeries (such as, for example, lumbar laminectomy or laminotomy when a robotic cutting bone is in use) or spinal cord damage due to the drill bit penetrating the bone.

Embodiments of the present disclosure provide technical solutions to one or more of the problems of (1) continuously or periodically monitoring a thickness of bone to be drilled, (2) preventing damage to soft tissue adjacent to hard tissue when drilling hard tissue, (3) monitoring separation of hard tissue and soft tissue during a surgical procedure; (4) providing a system for drilling and imaging an anatomical element; and (5) increasing patient safety by decreasing risk of damage to tissue surrounding a drilling site.

Figure 1B:
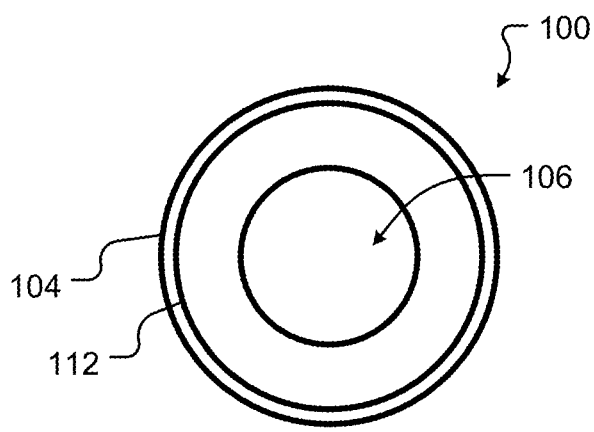
FIG. 1B is a cross-sectional top view of the system of FIG. 1A taken along A-A according to at least one embodiment of the present disclosure.

Turning first to FIGS. 1A-1B, a front view of a system 100 for drilling and imaging an anatomical element 102 and a top cross-sectional view taken along A-A of the system 100 are respectively shown. The system 100 is configured to drill the anatomical element 102 and image the anatomical element 102. By imaging the anatomical element 102, the system 100 can be used to determine a thickness of the anatomical element 102 (and more particularly, a thickness of hard tissue) and avoid drilling to an undesired depth that may penetrate the anatomical element 102 and damage surrounding tissue.

The system 100 comprises a housing 104 having a bore 106 and a surgical tool 108 (visible in FIGS. 2A-2B) disposed in the bore 106. The surgical tool 108 is operable to extend from the bore 106 through an opening 110 in the housing 104 and perform a surgical step. The surgical tool 108 may be automatically extended from the bore 106 by, for example, a controller such as a controller 724 described in FIG. 7. In some embodiments, the system 100 is oriented and/or operated by a robotic arm such as a robotic arm 716 described in FIG. 7. In some embodiments, the surgical tool 108 is a drill bit configured drill the anatomical element to form a borehole 116

Figure 6A:
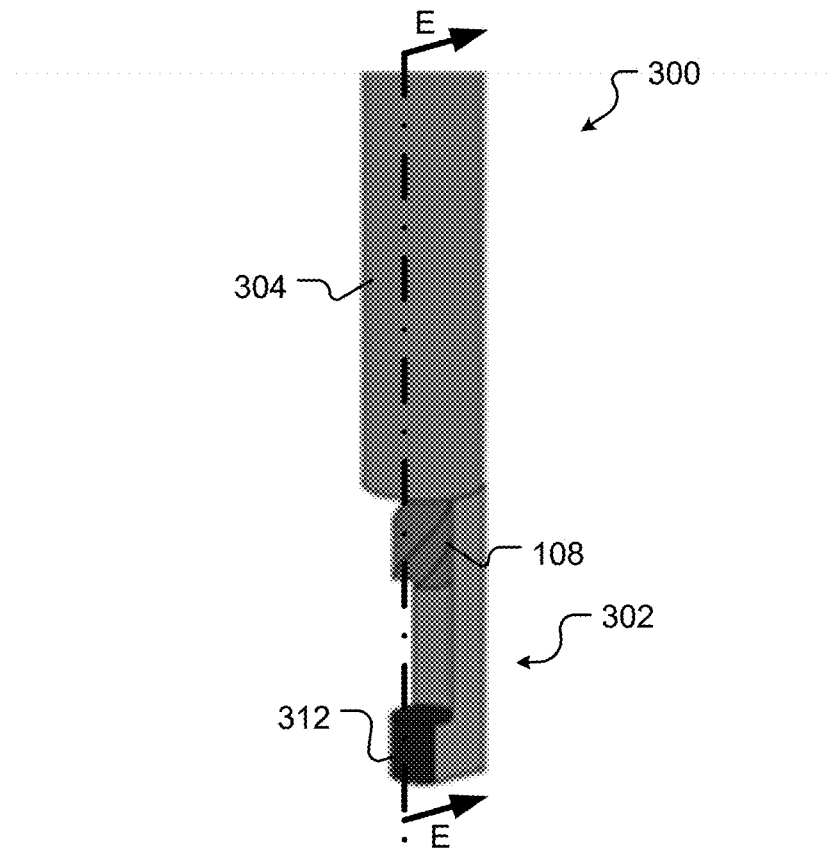
FIG. 6A is an isometric view of a system for milling and imaging according to at least one embodiment of the present disclosure.
Figure 6B:
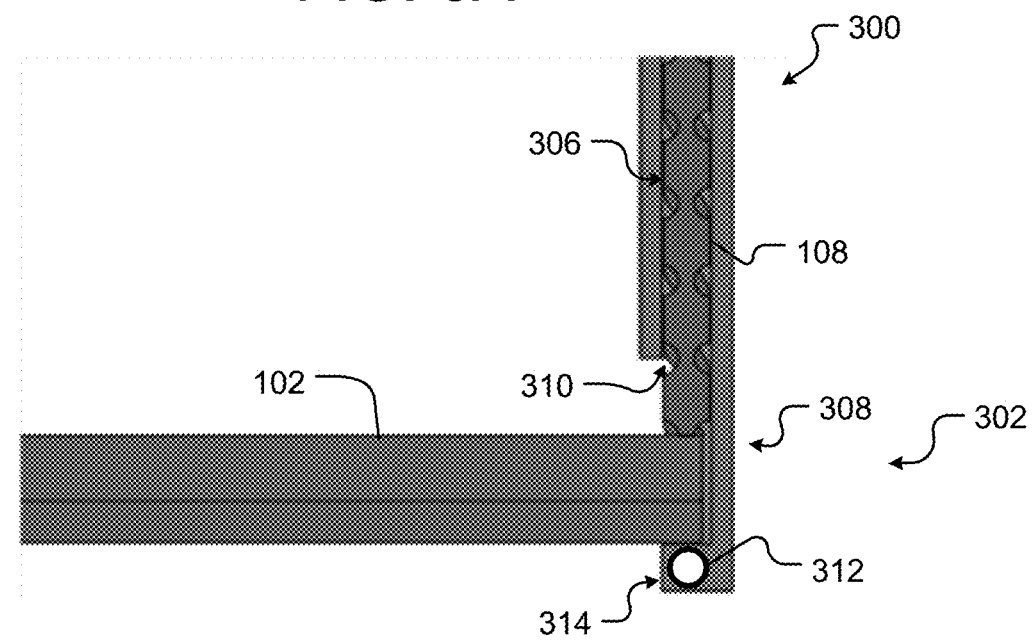
FIG. 6B is a cross-sectional side view of the system of FIG. 6A taken along E-E according to at least one embodiment of the present disclosure.
Figure 7:
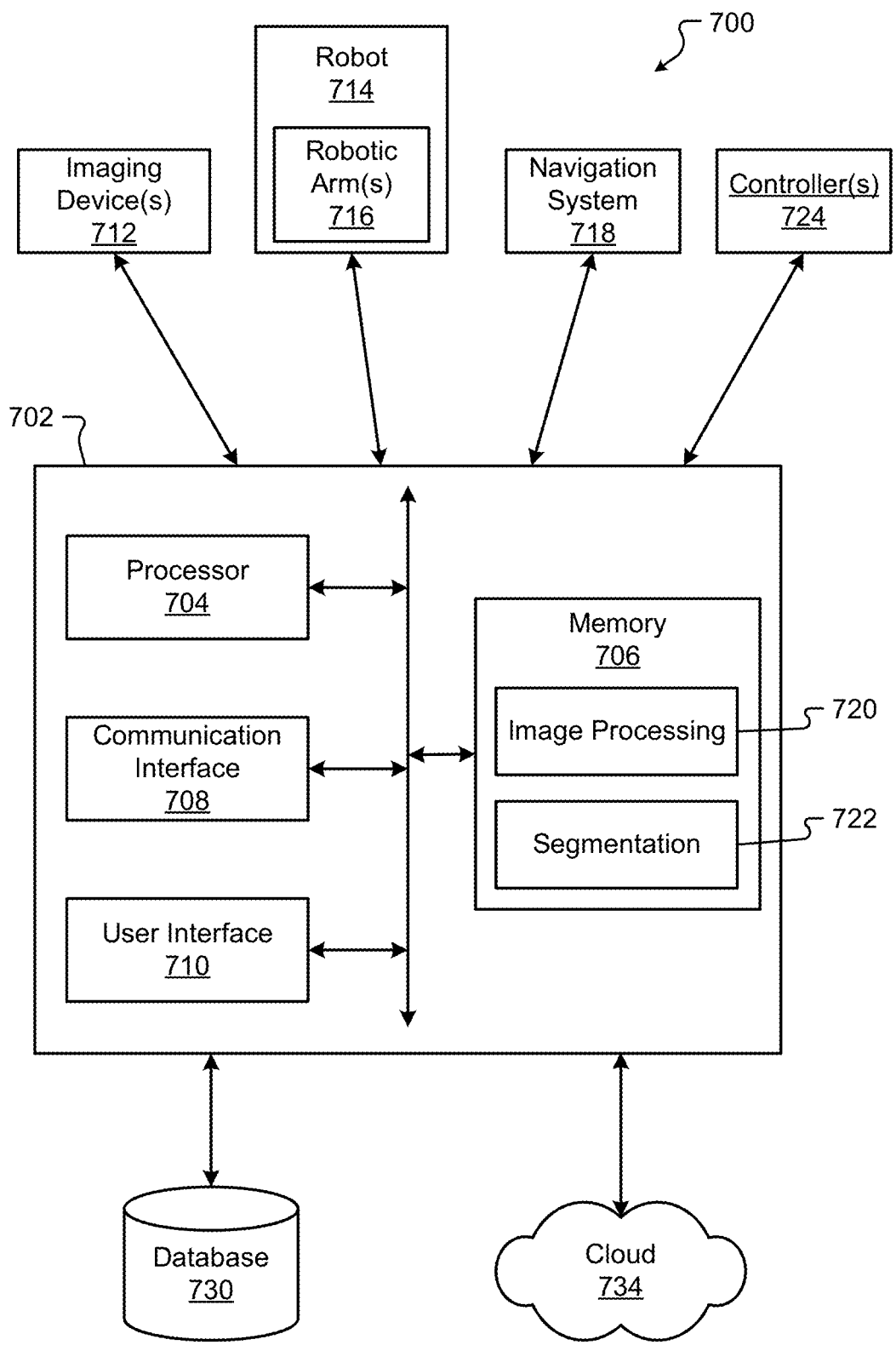
FIG. 7 is a block diagram of a system according to at least one embodiment of the present disclosure.

The system 100 also comprises an imaging device 112 (which may be the same as or similar to the imaging device 712 described in FIG. 7). In some embodiments, the imaging device 112 may be an ultrasound imaging device. In other embodiments, the imaging device 112 may be any imaging device capable of imaging the anatomical element. In some embodiments, such as shown in FIGS. 1A-2B, the imaging device 112 may be disposed at an end 114 of the housing 104. In other embodiments, such as shown in FIGS. 3A-5B, the imaging device 112 may be disposed in the bore 106. In still other embodiment, such as shown in FIGS. 6A-6B, the imaging device 112 may be disposed on an extension 302 extending from the housing 104. It will be appreciated that in other embodiments, the imaging device 112 may be attached to any portion of the housing 104, may be positioned anywhere in relation to the housing 104 and/or the bore 106, and/or may be a component separate from the housing 104. In still further embodiments, it will be appreciated that the imaging device 112 may be integrated with the surgical tool 108. For example, the imaging device 112 may be an ultrasound device integrated with a drill bit. In still other embodiments, it will be appreciated that the imaging device 112 may comprise two or more components (e.g., a transmitter and a receiver) and one component may be attached to the housing 104 or positioned in the bore 106 and another component may be a component separate from the housing 104.

In the illustrated embodiment, the imaging device 112 is positioned at the end 114 of the housing 104 and surrounds the bore 106. As shown, the imaging device 112 extends around an entire perimeter of the bore 106, however, it will be appreciated that in some embodiments the imaging device 112 may extend around a portion of the bore 106. Further, the imaging device 112 may extend around at least a portion of the bore 106 on any portion of the housing 104. The imaging device 112 has an inner diameter substantially equal to or greater than a diameter of the surgical tool 108 such that the surgical tool 108 can pass through the inner diameter when the surgical tool 108 is extended or retracted from the housing 104. Similarly, the bore 106 may have an inner diameter substantially equal to or greater than a diameter of the surgical tool 108 such that the surgical tool 108 can pass through the inner diameter when the surgical tool 108 is extended or retracted from the housing. In some embodiments the inner diameter of the imaging device 112 and the inner diameter of the bore 106 are substantially equal to each other. In other embodiments, the inner diameter of the imaging device 112 and the inner diameter of the bore 106 may be different from each other.

It will be appreciated that in some embodiments, a fluid source and/or a vacuum source may be provided. The fluid source may be configured to supply fluid to the bore 106 to irrigate the surgical tool 108 and/or the surgical site. In other embodiments, the fluid source may be configured to supply fluid directly to the surgical site. Such fluid may also increase an effectiveness of the imaging device 112, such as in embodiments where the imagining device 112 is an ultrasound device. In some embodiments, the vacuum source may be configured to provide a suction force to the bore to suction fluid from the surgical site through the bore. In other embodiments, the vacuum source may be configured to provide a suction force to fluid at the surgical site to remove the fluid from the surgical site. It will be appreciated that any of the system 100, 200, 300 described herein may include the fluid source and/or the vacuum source.

Figure 2A:
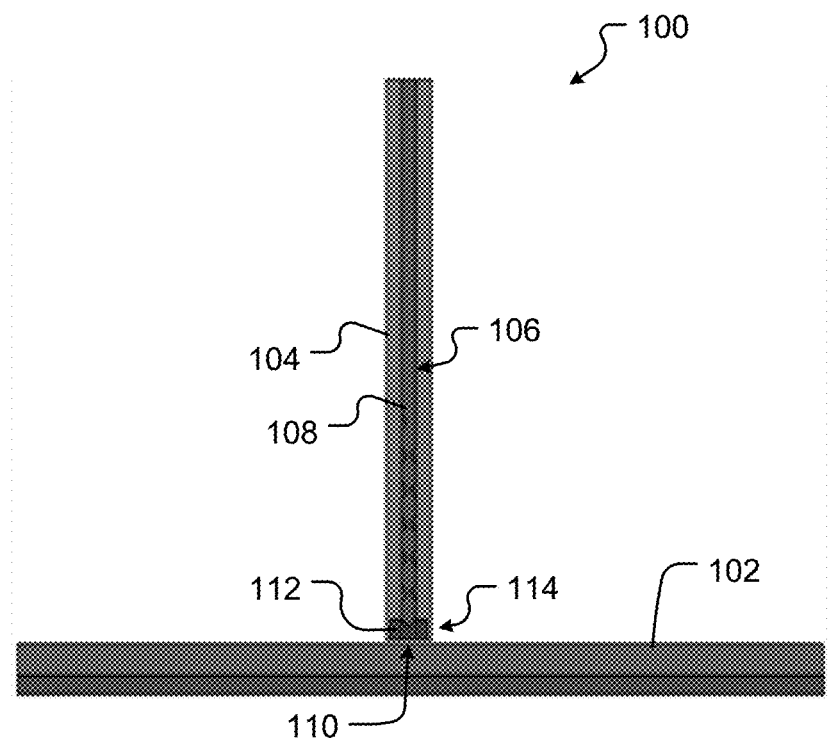
FIG. 2A is a cross-sectional side view of the system of FIG. 1A taken along B-B according to at least one embodiment of the present disclosure.
Figure 2B:
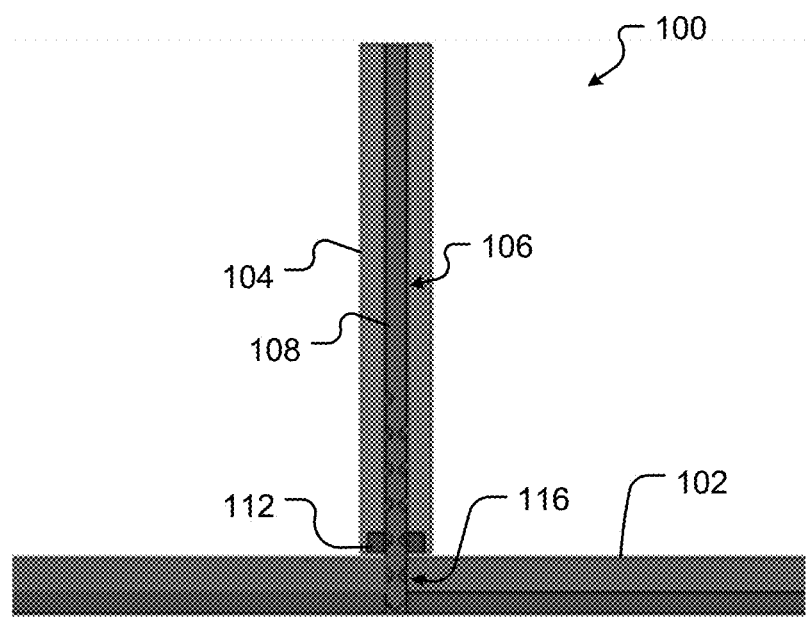
FIG. 2B is a cross-sectional side view of the system of FIG. 1A taken along B-B according to at least one embodiment of the present disclosure.

Turning to FIGS. 2A-2B, a side cross-sectional view taken along B-B of the system 100 in a first position and a second position are respectively shown. In FIG. 2A, the surgical tool 108 is shown in the first position wherein the system 100 is adjacent to the anatomical element 102 and the surgical tool 108 has not begun drilling the anatomical element 102. In FIG. 2B, the surgical tool 108 is shown in the second position wherein the surgical tool 108 has begun drilling the anatomical element 102. As shown, the surgical tool 108 may be movable between the first position and the second position.

Figure 8:
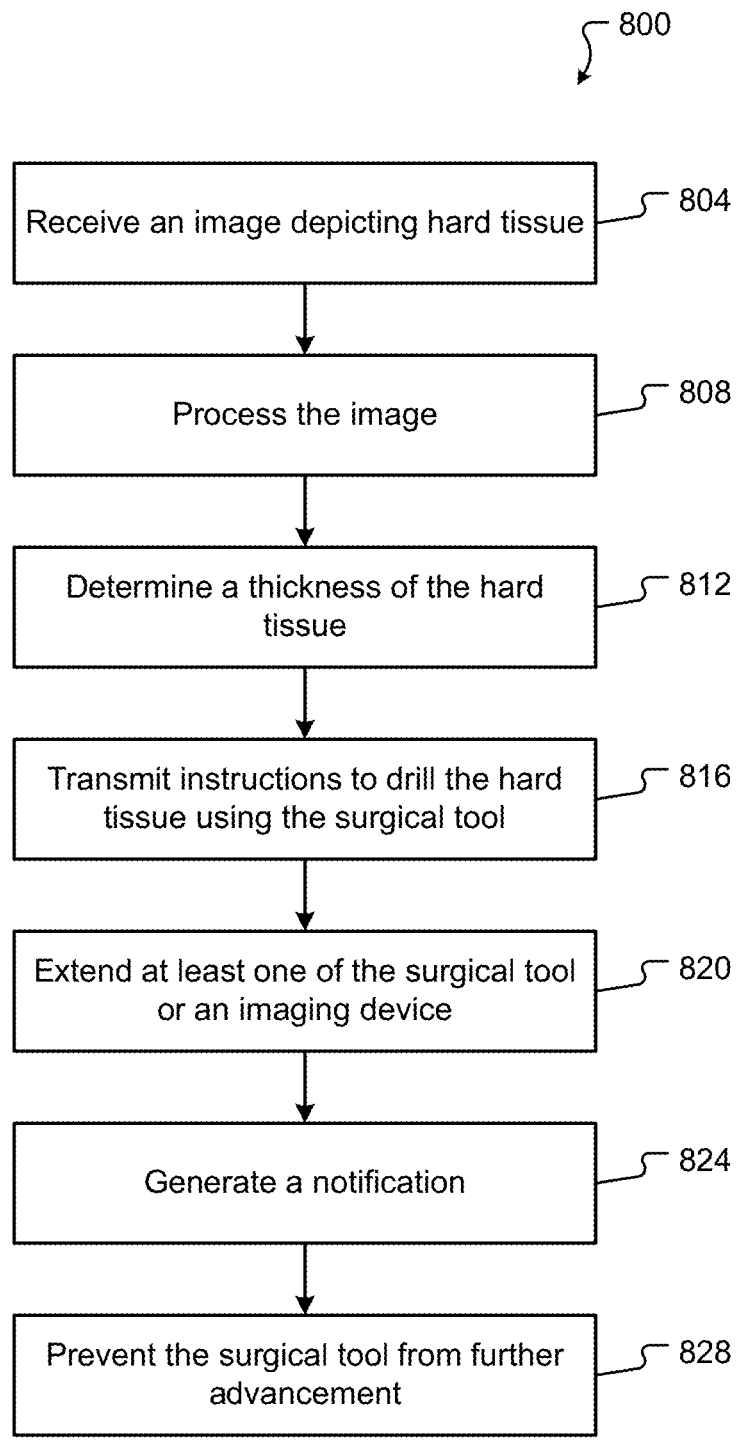
FIG. 8 is a flowchart according to at least one embodiment of the present disclosure.

As will also be described in detail in FIG. 8, the system 100 may be used to drill the anatomical element 102 using the surgical tool 108 (e.g., a drill bit). In some embodiments, the anatomical element may be hard tissue such as, for example, bone. The imaging device 112 may image the hard tissue continuously during drilling of the hard tissue, or periodically at certain time intervals. Such imaging may be used to determine a thickness of the hard tissue being drilled to prevent penetration of the hard tissue into adjacent soft tissue. Thus, once the thickness of the hard tissue reaches a threshold thickness, the surgical tool 108 may be stopped and removed from the anatomical element 102. As such, the imaging beneficially provides for increased safety when drilling hard tissue, and may prevent or eliminate damage to surrounding soft tissue by a surgical tool 108 such as a drill bit.

Figure 3A:
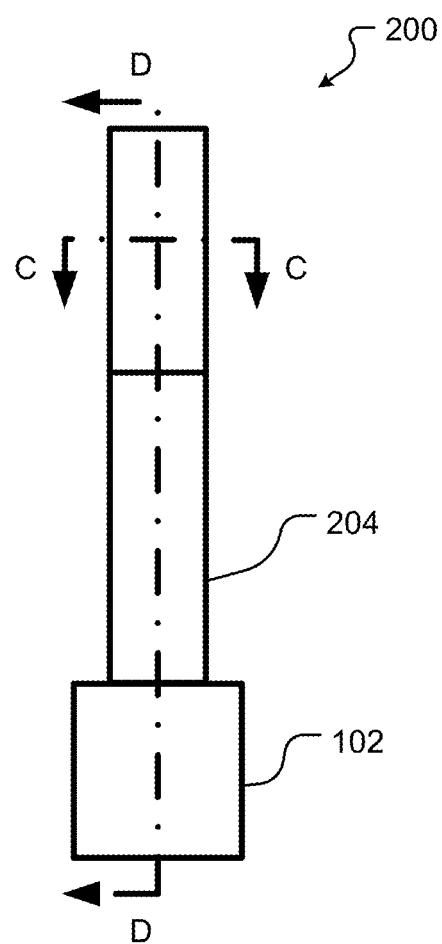
FIG. 3A is a front view of a system for drilling and imaging according to at least one embodiment of the present disclosure.
Figure 3B:
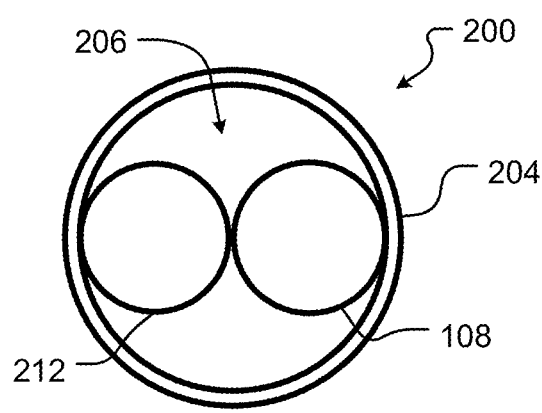
FIG. 3B is a cross-sectional top view of the system of FIG. 3A taken along C-C according to at least one embodiment of the present disclosure.

Turning to FIGS. 3A-3B, a front view of a system 200 for drilling and imaging an anatomical element 102 and a top cross-sectional view taken along C-C of the system 200 are respectively shown. The system 200 is also configured to drill the anatomical element 102 and image the anatomical element 102. In some embodiments, the system 300 may be oriented and/or operated by a robotic arm such as a robotic arm 716 described in FIG. 7. By imaging the anatomical element 102, the system 200 can also be used to determine a thickness of the anatomical element 102 and avoid drilling to an undesired depth that may penetrate the anatomical element 102 and damage surrounding tissue.

The system 200 is substantially similar to the system 100, except for the imaging device 212 is positioned in a bore 206 of a housing 204 adjacent to the surgical tool 108. Further, the imaging device 212 may, in some embodiments, include a flexible shaft for extending and retracting the imaging device 212. The bore 206 of the system 200 may have a variable diameter. For example, a diameter of the bore 206 at a first portion 214 may be at least substantially equal to or greater than a diameter of the surgical tool 108 and a diameter of the imaging device 212 combined and a diameter of the bore 206 at a second portion 216 (shown in FIGS. 4A-4C and 5A-5B) may be at least substantially equal to or greater than a diameter of the surgical tool 108 or a diameter of the imaging device 212. In other embodiments, the bore 206 may have the same diameter throughout a length of the bore 206. For example, a diameter of the bore 206 may be at least substantially equal to or greater than a diameter of the surgical tool 108 and a diameter of the imaging device 212 combined.

Figure 4A:
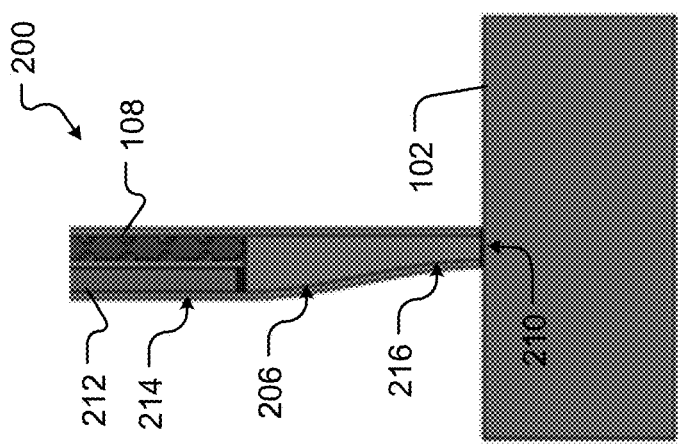
FIG. 4A is a cross-sectional side view of the system of FIG. 3A taken along D-D according to at least one embodiment of the present disclosure.
Figure 4B:
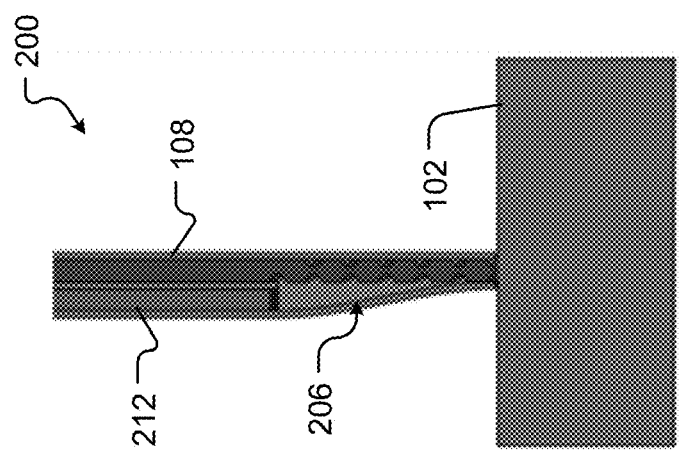
FIG. 4B is a cross-sectional side view of the system of FIG. 3A taken along D-D according to at least one embodiment of the present disclosure.
Figure 4C:
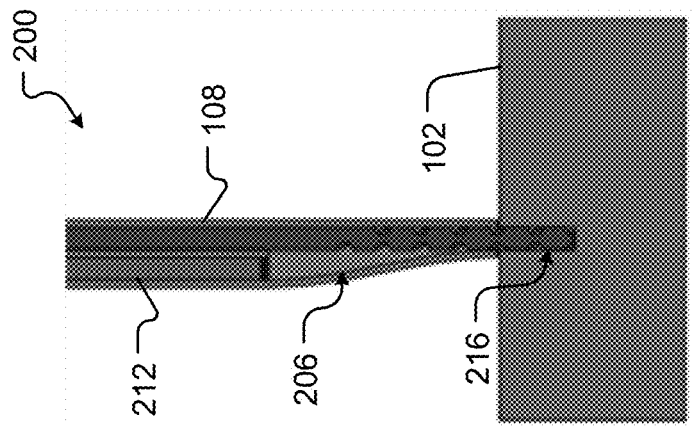
FIG. 4C is a cross-sectional side view of the system of FIG. 3A taken along D-D according to at least one embodiment of the present disclosure.

Turning to FIGS. 4A-4C, a side cross-sectional view taken along D-D of the system 200 wherein the surgical tool 108 is shown in a first position, a second position, and a third position, respectively. In FIG. 4A, the surgical tool 108 is shown in the first position wherein the system 100 is adjacent to the anatomical element 102 and the surgical tool 108 is retracted and positioned in the first portion 214 of the bore 206. In FIG. 2B, the surgical tool 108 is shown in the second position wherein the surgical tool 108 has been extended to an opening 210 of the housing 204 and is adjacent to the anatomical element 102. In FIG. 2C, the surgical tool 108 is shown drilling the anatomical element 102 to form a borehole 216 having a depth. Once the surgical tool 108 has completed drilling the borehole 216 to the depth, the surgical tool 108 may be retracted and moved to the first position wherein the surgical tool 108 is positioned in the first portion 214 of the bore 206. As shown, the surgical tool 108 is movable between the first position and the third position. It will be appreciated that the surgical tool 108 may be extendable to any past the housing 204.

Figure 5A:
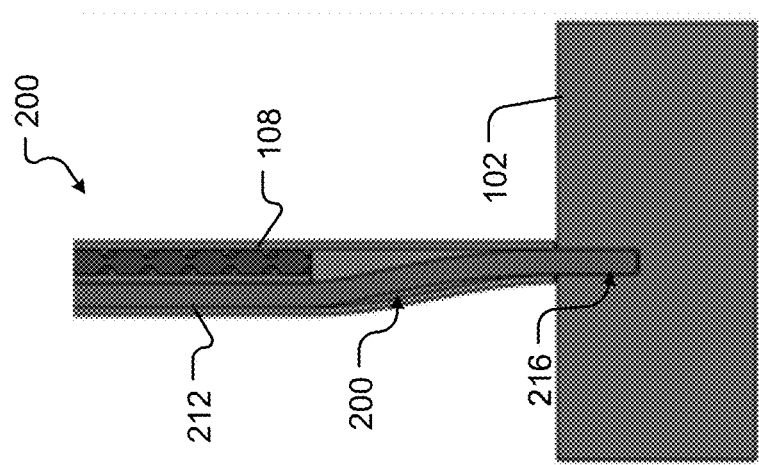
FIG. 5A is a cross-sectional side view of the system of FIG. 3A taken along D-D according to at least one embodiment of the present disclosure.
Figure 5B:
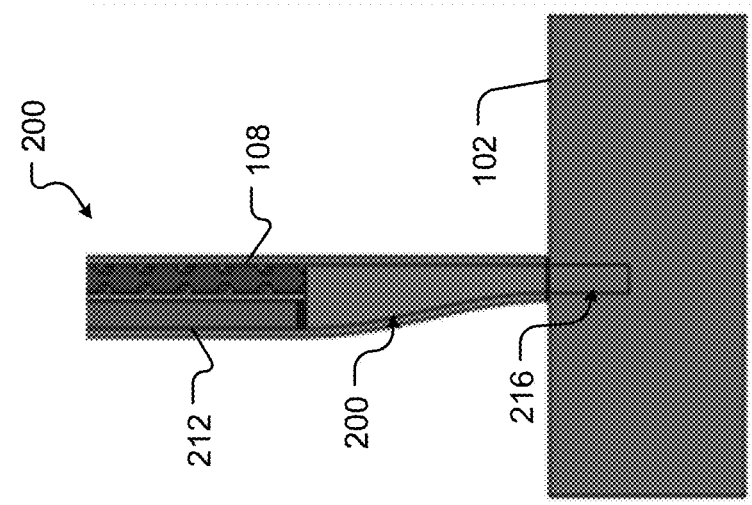
FIG. 5B is a cross-sectional side view of the system of FIG. 3A taken along D-D according to at least one embodiment of the present disclosure.

Turning to FIGS. 5A-5B, a side cross-sectional view taken along D-D of the system 200 wherein the imaging device 212 is shown in a first position and a second position, respectively. In FIG. 5A, the imaging device 212 is shown in the first position wherein the system 200 is adjacent to the borehole 216 and the imaging device 212 is retracted and positioned in the first portion 214 of the bore 206. In FIG. 5B, the imaging device 212 is shown in the second position wherein the imaging device 212 is extended and positioned in the borehole 216. The imaging device 212 may be used to obtain an image of the remaining hard tissue when in the second position. It will be appreciated that the imaging device 212 may be extended to any length past the housing 204. It will also be appreciated that the imaging device 212 may be extended to the anatomical element 102 prior to extending the surgical tool 108. For example, the imaging device 212 may be used to obtain an image of the anatomical element prior to drilling so as to determine an initial thickness of the anatomical element.

Figure 9:
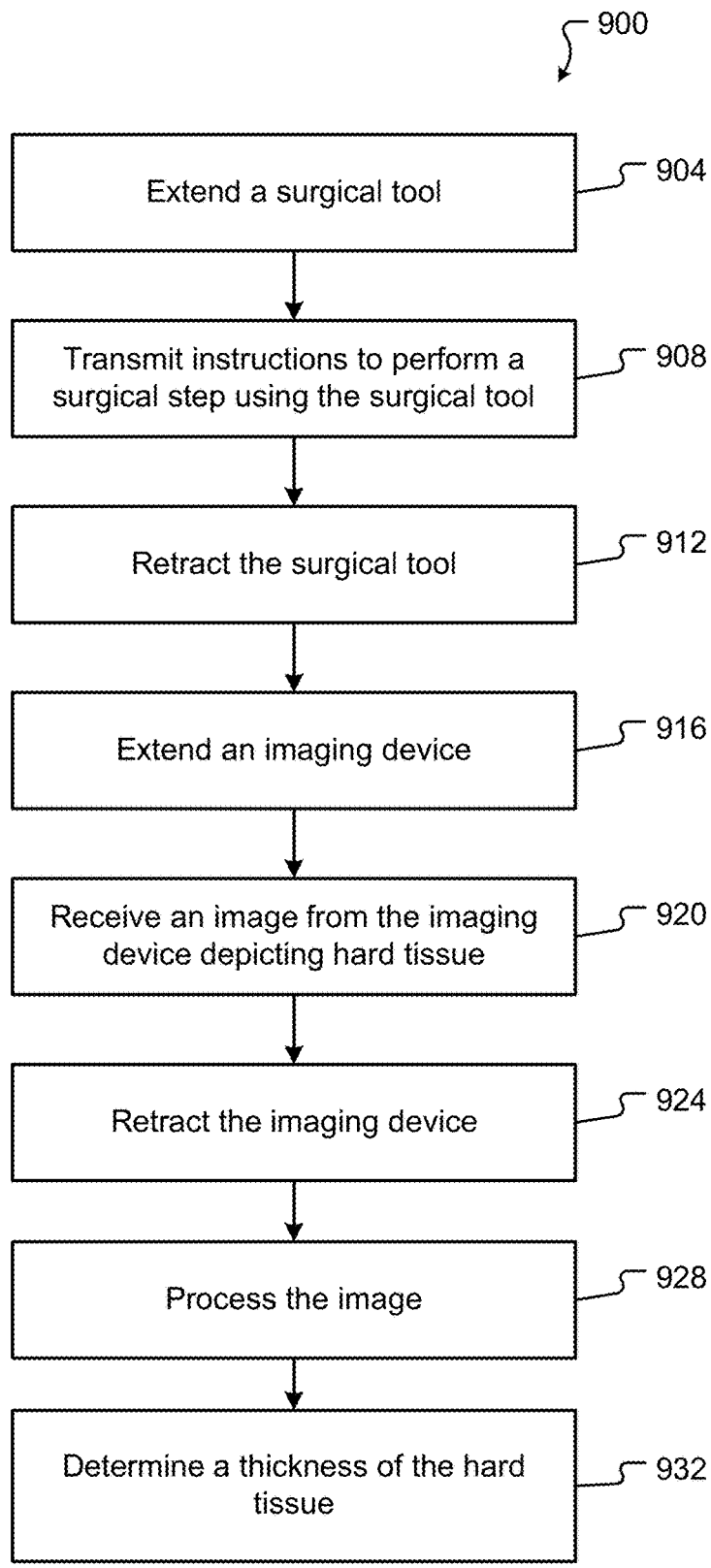
FIG. 9 is a flowchart according to at least one embodiment of the present disclosure.

As will also be described in detail in FIG. 9, the system 200 may be used to drill the anatomical element 102 using the surgical tool 108 (e.g., a drill bit). In some embodiments, the anatomical element may be hard tissue such as, for example, bone. The imaging device 212 may image the hard tissue periodically at certain time intervals. During such time intervals, the surgical tool 108 may be retracted from the borehole 216, the imaging device 212 may be extended into the borehole 216, and an image of the remaining anatomical element 102 may be obtained by the imaging device 212. Such imaging may be used to determine a remaining thickness of the hard tissue being drilled to prevent penetration of the hard tissue into adjacent soft tissue. Thus, once the thickness of the hard tissue reaches a threshold thickness, the surgical tool 108 may be stopped and removed from the anatomical element 102. As such and as previously described, the imaging beneficially provides for increased safety when drilling hard tissue, and may prevent or eliminate damage to surrounding soft tissue by a surgical tool 108 such as a drill bit.

Figure 6C:
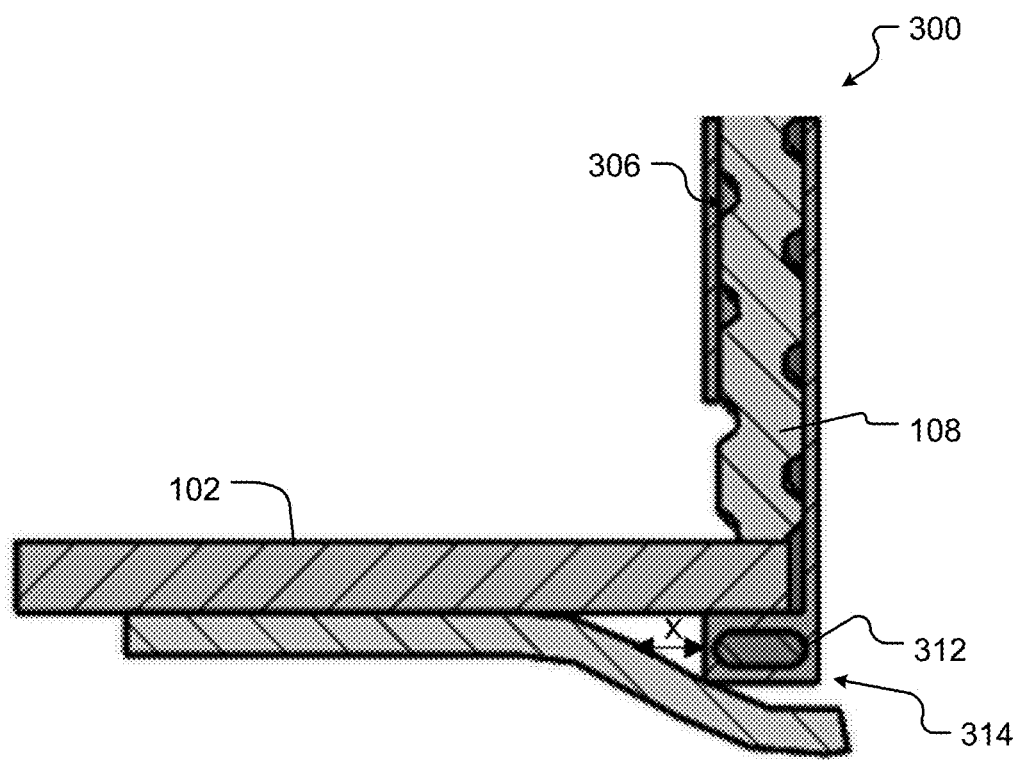
FIG. 6C is a cross-sectional side view of the system of FIG. 6A according to at least one embodiment of the present disclosure.

Turning to FIGS. 6A-6C, an isometric view of a system 300 for milling and imaging an anatomical element 102 and a side cross-sectional view taken along E-E of the system 300 are respectively shown. The system 300 is configured to mill the anatomical element 102, and more specifically, to cause separation between hard tissue and soft tissue such as during, for example, during a laminectomy or a laminotomy procedure. In such procedures, the hard tissue may be, for example, a lamina and the soft tissue may be, for example, dura matter. During such procedures, if the dura matter does not separate from the lamina (e.g., adhesion barrier may have occurred), then the procedure may be paused or stopped to use another surgical tool and/or perform a different surgical task to separate the dura matter from the lamina. The system 300 may then continue the initial procedure.

In some embodiments, the system 300 is oriented and/or operated by a robotic arm such as a robotic arm 716 described in FIG. 7. The system 300 comprises a housing 304 having a bore 306 (visible in FIG. 6B) and the surgical tool 108 is disposed in the bore 306. The surgical tool 108 is configured to extend from the bore 306 through an opening 310 in the housing 304. In some embodiments, the surgical tool 108 is a drill bit configured to mill the anatomical element 102. The housing 304 also includes an extension 302 extending from the housing 304. The extension 302 may, in some embodiments, comprise a first member 308 extending from the housing 304 and a second member 314 extending from and perpendicular to the first member 308. It will be appreciated that in other embodiments, the second member 314 may extend from the first member at any angle. In some embodiments, the second member 314 may be used to separate the soft tissue from the hard tissue. The second member 314 may also act as a shield to prevent the surgical tool 108 from contacting the soft tissue.

The system 300 also comprises an imaging device 312 (which may be the same as or similar to the imaging device 112, 212, 712). In some embodiments, the imaging device 312 may be an ultrasound imaging device. In other embodiments, the imaging device 312 may be any imaging device capable of imaging the anatomical element. In some embodiments the imaging device 312 is attached to the second member 314. In other embodiments, the imaging device 312 is integrated with the second member 314. The imaging device 312 may be used to image an anatomical element 102 comprising soft tissue and hard tissue. During such imaging, the soft tissue and the hard tissue may be positioned between the housing 304 and the extension 302. In other words, the hard tissue and the soft tissue may be positioned between the imaging device 312 and the surgical tool 108, as shown in FIG. 6B. In other embodiments, as shown in FIG. 6C, the second member 314 may be positioned between the hard tissue and the soft tissue and may be used to push the soft tissue away from the hard tissue, thereby separating the soft tissue and the hard tissue.

Figure 10:
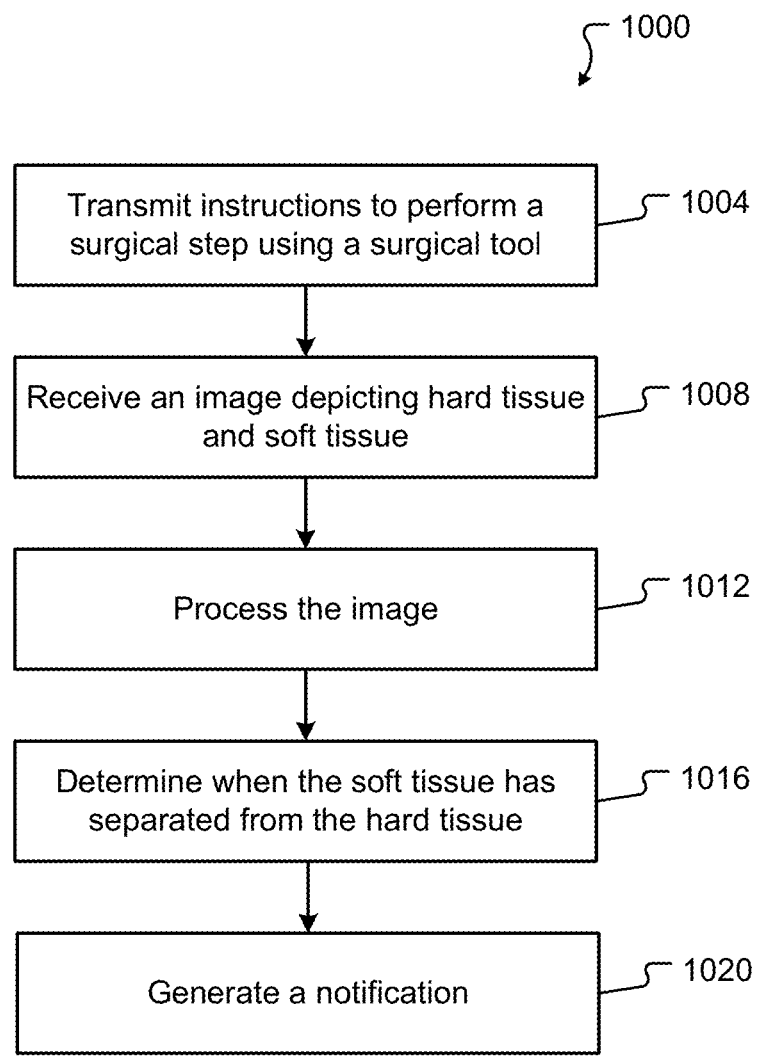
FIG. 10 is a flowchart according to at least one embodiment of the present disclosure.

As will also be described in detail in FIG. 10, the system 300 may be used to mill the hard tissue and to image the hard tissue and/or the soft tissue during a surgical procedure such as a laminectomy or a laminotomy. Images obtained from the imaging device 312 (whether periodically or continuously) may be used to monitor separation of the hard tissue and the soft tissue during the surgical procedure. More specifically, as shown in FIG. 6C, a soft tissue distance X between soft tissue and the imaging device 312 (and the second member 314) is shown. When separation occurs, soft tissue may be further from the imaging device 312 and the soft tissue distance X may be greater than the soft tissue distance X when separation does not occur. For example, the soft tissue distance X may be greater than 10 mm when separation occurs and the soft tissue distance X may be less than 5 mm when separation does not occur. It will be appreciated that in some embodiments the soft tissue distance X may be greater than 1 mm or 5 mm. It will also be appreciated that in some embodiments, the soft tissue distance X may be less than 10 mm or 1 mm.

Turning to FIG. 7, a block diagram of a system 700 according to at least one embodiment of the present disclosure is shown. The system 700 may be used with the system 100, 200, and/or 300 to drill or mill hard tissue and image the hard tissue and/or adjacent soft tissue soft tissue and/or carry out one or more other aspects of one or more of the methods disclosed herein. The system 700 comprises a computing device 702, one or more imaging devices 712, a robot 714, a navigation system 718, a controller 724, a database 730, and/or a cloud or other network 734. Systems according to other embodiments of the present disclosure may comprise more or fewer components than the system 700. For example, the system 700 may not include the imaging device 712, the robot 714, the navigation system 718, the controller 724, one or more components of the computing device 702, the database 730, and/or the cloud 734.

The computing device 702 comprises a processor 704, a memory 706, a communication interface 708, and a user interface 710. Computing devices according to other embodiments of the present disclosure may comprise more or fewer components than the computing device 702.

The processor 704 of the computing device 702 may be any processor described herein or any similar processor. The processor 704 may be configured to execute instructions stored in the memory 706, which instructions may cause the processor 704 to carry out one or more computing steps utilizing or based on data received from the imaging device 712, the robot 714, the navigation system 718, the database 730, and/or the cloud 734.

The memory 706 may be or comprise RAM, DRAM, SDRAM, other solid-state memory, any memory described herein, or any other tangible, non-transitory memory for storing computer-readable data and/or instructions. The memory 706 may store information or data useful for completing, for example, any step of the methods 800, 900, and/or 1000 described herein, or of any other methods. The memory 706 may store, for example, instructions and/or machine learning models that support one or more functions of the robot 714. For instance, the memory 706 may store content (e.g., instructions and/or machine learning models) that, when executed by the processor 704, enable image processing 720 and/or segmentation 722.

The image processing 720 enables the processor 704 to process image data of an image (obtained from, for example, the imaging device 112, 212, 312, 712) for the purpose of, for example, identifying information about anatomical elements and/or objects depicted in the image. The information may comprise, for example, identification of hard tissue and/or soft tissues, a boundary between hard tissue and soft tissue, a boundary of hard tissue and/or soft tissue, identification of a surgical tool such as the surgical tool 108, etc. The image processing 720 may, for example, identify hard tissue, soft tissue, and/or a boundary of the hard tissue and/or soft tissue by determining a difference in or contrast between colors or grayscales of image pixels. For example, a boundary between the hard tissue and the soft tissue may be identified as a contrast between lighter pixels and darker pixels. The imaging processing 720 may also use segmentation 722, as described below.

The segmentation 722 enables the processor 704 to segment the image data so as to identify individual objects and/or anatomical elements in the image. The segmentation 722 may enable the processor 704 to identify a boundary of an object or an anatomical element by using, for example, feature recognition. For example, the segmentation 722 may enable the processor 704 to identify a vertebra in image data. In other instances, the segmentation 722 may enable the processor 704 to identify a boundary of an object or an anatomical element by determining a difference in or contrast between colors or grayscales of image pixels.

Content stored in the memory 706, if provided as in instruction, may, in some embodiments, be organized into one or more applications, modules, packages, layers, or engines. Alternatively or additionally, the memory 706 may store other types of content or data (e.g., machine learning models, artificial neural networks, deep neural networks, etc.) that can be processed by the processor 704 to carry out the various method and features described herein. Thus, although various contents of memory 706 may be described as instructions, it should be appreciated that functionality described herein can be achieved through use of instructions, algorithms, and/or machine learning models. The data, algorithms, and/or instructions may cause the processor 704 to manipulate data stored in the memory 706 and/or received from or via the imaging device 712, the robot 714, the database 730, and/or the cloud 734.

The computing device 702 may also comprise a communication interface 708. The communication interface 708 may be used for receiving image data or other information from an external source (such as the imaging device 712, the robot 714, the navigation system 718, the database 730, the cloud 734, and/or any other system or component not part of the system 700), and/or for transmitting instructions, images, or other information to an external system or device (e.g., another computing device 702, the imaging device 712, the robot 714, the navigation system 718, the database 730, the cloud 734, and/or any other system or component not part of the system 700). The communication interface 708 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 708 may be useful for enabling the device 702 to communicate with one or more other processors 704 or computing devices 702, whether to reduce the time needed to accomplish a computing-intensive task or for any other reason.

The computing device 702 may also comprise one or more user interfaces 710. The user interface 710 may be or comprise a keyboard, mouse, trackball, monitor, television, screen, touchscreen, and/or any other device for receiving information from a user and/or for providing information to a user. The user interface 710 may be used, for example, to receive a user selection or other user input regarding any step of any method described herein. Notwithstanding the foregoing, any required input for any step of any method described herein may be generated automatically by the system 700 (e.g., by the processor 704 or another component of the system 700) or received by the system 700 from a source external to the system 700. In some embodiments, the user interface 710 may be useful to allow a surgeon or other user to modify instructions to be executed by the processor 704 according to one or more embodiments of the present disclosure, and/or to modify or adjust a setting of other information displayed on the user interface 710 or corresponding thereto.

Although the user interface 710 is shown as part of the computing device 702, in some embodiments, the computing device 702 may utilize a user interface 710 that is housed separately from one or more remaining components of the computing device 702. In some embodiments, the user interface 710 may be located proximate one or more other components of the computing device 702, while in other embodiments, the user interface 710 may be located remotely from one or more other components of the computer device 702.

The imaging device 712 may be operable to image anatomical feature(s) (e.g., a bone, veins, tissue, etc.) and/or other aspects of patient anatomy to yield image data (e.g., image data depicting or corresponding to a bone, veins, tissue, etc.). The imaging device 712 may be the same as or similar to the imaging device 112, 212, 312. "Image data" as used herein refers to the data generated or captured by an imaging device 712, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 712 may be used to obtain first image data (e.g., a first image) at a first time, and a second imaging device 712 may be used to obtain second image data (e.g., a second image) at a second time after the first time. The imaging device 712 may be capable of taking a 2D image or a 3D image to yield the image data. The imaging device 712 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 712 suitable for obtaining images of an anatomical feature of a patient. The imaging device 712 may be contained entirely within a single housing, or may comprise a transmitter/emitter and a receiver/detector that are in separate housings or are otherwise physically separated.

In some embodiments, the imaging device 712 may comprise more than one imaging device 712. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 712 may be operable to generate a stream of image data. For example, the imaging device 712 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

As previously described, the image data, once processed by, for example, the processor 704 using image processing 720 and/or segmentation 722, may be used to determine a thickness of hard tissue to be drilled. In some embodiments, the image data may be used to monitor separation of hard tissue and soft tissue. The image data may enable, for example, a robot 714 to determine whether to continue drilling and/or milling hard tissue based a remaining thickness of hard tissue and/or separation of hard tissue and soft tissue, respectively.

The robot 714 may be any surgical robot or surgical robotic system. The robot 714 may be or comprise, for example, the Mazor X™ Stealth Edition robotic guidance system. The robot 714 may be configured to position the system 100, 200, 300 at one or more precise position(s) and orientation(s), and/or to return the imaging device 712 to the same position(s) and orientation(s) at a later point in time. The robot 714 may additionally or alternatively be configured to manipulate a surgical tool (whether based on guidance from the navigation system 718 or not) to accomplish or to assist with a surgical task. In some embodiments, the robot 714 may be configured to hold and/or manipulate an anatomical element during or in connection with a surgical procedure. The robot 714 may comprise one or more robotic arms 716. In some embodiments, the robotic arm 716 may comprise a first robotic arm and a second robotic arm, though the robot 714 may comprise more than two robotic arms. In some embodiments, one or more of the robotic arms 716 may be used to hold and/or maneuver the imaging device 712. In embodiments where the imaging device 712 comprises two or more physically separate components (e.g., a transmitter and receiver), one robotic arm 716 may hold one such component, and another robotic arm 716 may hold another such component. Each robotic arm 716 may be positionable independently of the other robotic arm. The robotic arms 716 may be controlled in a single, shared coordinate space, or in separate coordinate spaces.

The robot 714, together with the robotic arm 716, may have, for example, one, two, three, four, five, six, seven, or more degrees of freedom. Further, the robotic arm 716 may be positioned or positionable in any pose, plane, and/or focal point. The pose includes a position and an orientation. As a result, an imaging device 712, surgical tool, or other object held by the robot 714 (or, more specifically, by the robotic arm 716) may be precisely positionable in one or more needed and specific positions and orientations.

The robotic arm(s) 716 may comprise one or more sensors that enable the processor 704 (or a processor of the robot 714) to determine a precise pose in space of the robotic arm (as well as any object or element held by or secured to the robotic arm).

In some embodiments, reference markers (e.g., navigation markers) may be placed on the robot 714 (including, e.g., on the robotic arm 716), the system 100, 200, 300, the imaging device 712, or any other object in the surgical space. The reference markers may be tracked by the navigation system 718, and the results of the tracking may be used by the robot 714 and/or by an operator of the system 700 or any component thereof. In some embodiments, the navigation system 718 can be used to track other components of the system (e.g., imaging device 712) and the system can operate without the use of the robot 714 (e.g., with the surgeon manually manipulating the imaging device 712 and/or one or more surgical tools, based on information and/or instructions generated by the navigation system 718, for example).

In the illustrated embodiment, the system 700 includes the controller 724, though in some embodiments the system 700 may not include the controller 724. The controller 724 may be an electronic, a mechanical, or an electro-mechanical controller. The controller 724 may comprise or may be any processor described herein. The controller 724 may comprise a memory storing instructions for executing any of the functions or methods described herein as being carried out by the controller 724. In some embodiments, the controller 724 may be configured to simply convert signals received from the computing device 702 (e.g., via a communication interface 108) into commands for operating the system 100, 200, 300 (and more specifically, for actuating the surgical tool 108 and/or the imaging device 112, 212, 312, 712), the navigation system 718, and/or the robot 714. In other embodiments, the controller 724 may be configured to process and/or convert signals received from the system 100, 200, 300, the navigation system 718, and/or the robot 714. Further, the controller 724 may receive signals from one or more sources (e.g., the system 100, 200, 300, the navigation system 718, and/or the robot 714) and may output signals to one or more sources.

The navigation system 718 may provide navigation for a surgeon and/or a surgical robot during an operation. The navigation system 718 may be any now-known or future-developed navigation system, including, for example, the Medtronic StealthStation™ S8 surgical navigation system or any successor thereof. The navigation system 718 may include one or more cameras or other sensor(s) for tracking one or more reference markers, navigated trackers, or other objects within the operating room or other room in which some or all of the system 700 is located. The one or more cameras may be optical cameras, infrared cameras, or other cameras. In some embodiments, the navigation system 718 may comprise one or more electromagnetic sensors. In various embodiments, the navigation system 718 may be used to track a position and orientation (e.g., a pose) of the system 100, 200, 300, the imaging device 712, the robot 714 and/or robotic arm 716, and/or one or more surgical tools (or, more particularly, to track a pose of a navigated tracker attached, directly or indirectly, in fixed relation to the one or more of the foregoing). The navigation system 718 may include a display for displaying one or more images from an external source (e.g., the computing device 702, imaging device 712, or other source) or for displaying an image and/or video stream from the one or more cameras or other sensors of the navigation system 718. In some embodiments, the system 700 can operate without the use of the navigation system 718. The navigation system 718 may be configured to provide guidance to a surgeon or other user of the system 700 or a component thereof, to the robot 714, or to any other element of the system 700 regarding, for example, a pose of one or more anatomical elements, whether or not a tool is in the proper trajectory, and/or how to move a tool into the proper trajectory to carry out a surgical task according to a preoperative or other surgical plan.

The database 730 may store information that correlates one coordinate system to another (e.g., one or more robotic coordinate systems to a patient coordinate system and/or to a navigation coordinate system). The database 730 may additionally or alternatively store, for example, one or more surgical plans (including, for example, pose information about a target and/or image information about a patient's anatomy at and/or proximate the surgical site, for use by the robot 714, the navigation system 718, and/or a user of the computing device 702 or of the system 700); one or more images useful in connection with a surgery to be completed by or with the assistance of one or more other components of the system 700; and/or any other useful information. The database 730 may be configured to provide any such information to the computing device 702 or to any other device of the system 700 or external to the system 700, whether directly or via the cloud 734. In some embodiments, the database 730 may be or comprise part of a hospital image storage system, such as a picture archiving and communication system (PACS), a health information system (HIS), and/or another system for collecting, storing, managing, and/or transmitting electronic medical records including image data.

The cloud 734 may be or represent the Internet or any other wide area network. The computing device 702 may be connected to the cloud 734 via the communication interface 708, using a wired connection, a wireless connection, or both. In some embodiments, the computing device 702 may communicate with the database 730 and/or an external device (e.g., a computing device) via the cloud 734.

The system 700 or similar systems may be used, for example, to carry out one or more aspects of any of the methods 800, 900, and/or 1000 described herein. The system 700 or similar systems may also be used for other purposes.

FIG. 8 depicts a method 800 that may be used, for example, for drilling and imaging an anatomical element.

The method 800 (and/or one or more steps thereof) may be carried out or otherwise performed, for example, by at least one processor. The at least one processor may be the same as or similar to the processor(s) 704 of the computing device 702 described above. The at least one processor may be part of a robot (such as a robot 714) or part of a navigation system (such as a navigation system 718). A processor other than any processor described herein may also be used to execute the method 800. The at least one processor may perform the method 800 by executing elements stored in a memory such as the memory 706. The elements stored in the memory and executed by the processor may cause the processor to execute one or more steps of a function as shown in method 800. One or more portions of a method 800 may be performed by the processor executing any of the contents of memory, such as an image processing 720 and/or a segmentation 722.

The method 800 comprises receiving an image depicting hard tissue (step 804). In some embodiments, the image may also depict soft tissue. The image may be received from, for example, an imaging device such as the imaging device 112, 212, 312, 712 of a system such as the system 100, 200. The imaging device may be, for example, an ultrasound device.

The system may comprise a housing such as the housing 104, 204 having a bore such as the bore 106, 206 and an opening such as the opening 110, 210. The system may also comprise a surgical tool such as the surgical tool 108 disposed in the bore and operable to extend from the bore and through the opening. The surgical tool is also configured to, for example, drill or mill an anatomical element such as the anatomical element 102.

The imaging device in some embodiments surrounds at least a portion of the bore. In at least some of the embodiments, the imaging device surrounds the perimeter of the bore. In other embodiments, the imaging device is disposed in the bore and adjacent to the surgical tool. In such embodiments, the imaging device is operable to extend from the bore and through the opening.

The method 800 also comprises processing the image (step 808). Processing the image may comprise a processor such as the processor 704 using image processing such as the image processing 720 to identify information about anatomical elements and/or objects depicted in the image. More specifically, the image processing may enable the processor to identify hard tissue and/or soft tissue and boundaries of the hard tissue and/or soft tissue. Such identification may occur by, for example, determining a difference in or contrast between colors or grayscales of image pixels. For example, a boundary between the hard tissue and the soft tissue may be identified as a contrast between lighter pixels and darker pixels. The imaging processing may also use segmentation such as the segmentation 722.

The segmentation enables the processor to segment the image data so as to identify individual objects and/or anatomical elements in the image. The segmentation may enable the processor to identify a boundary of an object or an anatomical element by using, for example, feature recognition. For example, the segmentation may enable the processor to identify a vertebra in image data. In other instances, the segmentation may enable the processor to identify a boundary of an object or an anatomical element by determining a difference in or contrast between colors or grayscales of image pixels.

Processing the image to identify the hard tissue and/or soft tissue enables measurements of the hard tissue and/or soft tissue such as, for example, a thickness, a volume (in cases of three-dimensional representations), a shape, and/or size of the hard tissue and/or soft tissue.

The method 800 also comprises determining a thickness of the hard tissue (step 812). Determining the thickness of the hard tissue may comprise identifying, for example, a borehole formed by the surgical tool in the hard tissue identified in the step 808 and measuring a remaining thickness of the hard tissue at a bottom of the borehole to the soft tissue. It will be appreciated that in some embodiments, the step 812 may occur prior to performing any surgical step to determine an initial thickness of the hard tissue. In other embodiments, the step 812 may occur after a borehole has been formed by the surgical tool, such as in step 816 described below.

The method 800 also comprises transmitting instructions to drill the hard tissue using the surgical tool (step 816). The instructions may be automatically generated and transmitted by, for example, the processor. The instructions may be generated and transmitted when the thickness determined in the step 812 does not meet or exceed a thickness threshold. Such thickness threshold will be described in detail in step 824 below.

In some embodiments, the instructions may be transmitted to a controller such as the controller 724 or a robot such as the robot 714. In some embodiments, the robot may orient the surgical tool at the surgical site. The controller and/or the robot may control the surgical tool to drill the hard tissue for a predetermined duration of time or for a predetermined distance as defined by the instructions. In other embodiments, the instructions may be displayed on, for example, a user interface such as the user interface 710 to instruct a user, such as a surgeon or other medical provider, to drill the hard tissue using the surgical tool.

The method 800 also comprises extending at least one of the surgical tool or the imaging device (step 820). In some embodiments, the controller may control the surgical tool and/or the imaging device to extend the surgical tool and/or the imaging device. More specifically, the controller may control, for example, a motor configured to extend and/or retract the surgical tool and/or the imaging device. In some embodiments, the surgical tool and the imaging device may be extended or retracted simultaneously. In other embodiments the surgical tool and/or the imaging device may be separately extended or retracted.

The method 800 also comprises generating a notification (step 824). The notification may be a visual notification, an audible notification, or any type of notification communicated to a user. The notification may be communicated to the user via a user interface such as the user interface 710. In some embodiments, the notification may be automatically generated by the processor 704. In other embodiments, the notification may be automatically generated by any component of a system such as the system 700. The notification may, for example, prompt a user such as a surgeon or other medical provider to end the surgical step and/or remove the system from the surgical site.

The notification may be generated when the determined thickness of the hard tissue as determined in, for example, the step 812 above has reached or exceeded a predetermined thickness threshold. The thickness threshold may correlate to a maximum allowable thickness of the hard tissue to prevent undesired penetration of the hard tissue (and thus, exposure to the adjacent soft tissue). The thickness threshold may be determined automatically using artificial intelligence and training data (e.g., historical cases) in some embodiments. In other embodiments, the thickness threshold may be or comprise, or be based on, surgeon input received via the user interface. In further embodiments, the thickness threshold may be determined automatically using artificial intelligence, and may thereafter be reviewed and approved (or modified) by a surgeon or other user.

It will be appreciated that in some embodiments, the method 800 may not include the step 824.

The method 800 also comprises preventing the surgical tool from further advancement (step 828). The surgical tool may be prevented from further advancement when the thickness of the hard tissue determined in, for example, the step 812, has met or exceeded the thickness threshold. In some embodiments, a motor may control the surgical tool and a brake may be applied to the motor to prevent the surgical tool from further advancement. In other embodiments, instructions may be generated and transmitted to, for example, the controller to prevent the surgical tool from further advancement.

It will be appreciated that in some embodiments, the method 800 may not include the step 828.

It will be appreciated that in some embodiments, the steps 804-812 may be continuously repeated or periodically executed at a time interval. The steps 804-812 may also be executed based on user input. The step 804-812 may be used to monitor a thickness of hard tissue being drilled to ensure that a surgical tool such as, for example, a drill bit does not penetrate the hard tissue and damage adjacent soft tissue. The step 816 may also be repeated until a desired depth of a borehole is achieved and/or until the thickness of the hard tissue meets or exceeds a thickness threshold.

The present disclosure encompasses embodiments of the method 800 that comprise more or fewer steps than those described above, and/or one or more steps that are different than the steps described above.

FIG. 9 depicts a method 900 that may be used, for example, for drilling and imaging an anatomical element.

The method 900 (and/or one or more steps thereof) may be carried out or otherwise performed, for example, by at least one processor. The at least one processor may be the same as or similar to the processor(s) 704 of the computing device 702 described above. The at least one processor may be part of a robot (such as a robot 714) or part of a navigation system (such as a navigation system 718). A processor other than any processor described herein may also be used to execute the method 900. The at least one processor may perform the method 900 by executing elements stored in a memory such as the memory 706. The elements stored in memory and executed by the processor may cause the processor to execute one or more steps of a function as shown in method 900. One or more portions of a method 900 may be performed by the processor executing any of the contents of memory, such as an image processing 720 and/or a segmentation 722.

The method 900 comprises extending a surgical tool (step 904). The step 904 may be the same as or similar to the step 820 of the method 800 described above as applied to the surgical tool. Extending the surgical tool may extend the surgical tool to a surface of an anatomical element such as the anatomical element 102 or into an existing borehole that may have been formed by, for example, the surgical tool or a different surgical tool.

The surgical tool may be the same as or similar to the surgical tool 108 of a system such as the system 200. The system may comprise a housing such as the housing 204 having a bore such as the bore 206 and an opening such as the opening 210. The system may also comprise a surgical tool such as the surgical tool 108 disposed in the bore and operable to extend from the bore and through the opening. The surgical tool is also configured to, for example, drill an anatomical element such as the anatomical element 102.

In some embodiments, an imaging device such as the imaging device 212 is disposed in the bore and adjacent to the surgical tool. In such embodiments, the imaging device is operable to extend from the bore and through the opening. The bore may have a variable diameter. For example, a diameter of the bore at a first portion such as the first portion 214 may be at least substantially equal to or greater than a diameter of the surgical tool and a diameter of the imaging device combined and a diameter of the bore at a second portion such as the second portion 216 may be at least substantially equal to or greater than a diameter of the surgical tool or a diameter of the imaging device. In other embodiments, the bore may have the same diameter throughout a length of the bore. For example, a diameter of the bore may be at least substantially equal to or greater than a diameter of the surgical tool and a diameter of the imaging device combined.

The method 900 also comprises transmitting instructions to perform a surgical step using the surgical tool (step 908). The step 908 may be the same as or similar to the step 816 of the method 800 describe above. The surgical tool may perform a surgical step such as, for example, drilling and forming a borehole in the anatomical element. In some embodiments the surgical tool may be, for example, a drill bit, and the anatomical element may be, for example, hard tissue.

The method 900 also comprises retracting the surgical tool (step 912). In some embodiments, the controller may control the surgical tool and/or the imaging device to retract the surgical tool and/or the imaging device. More specifically, the controller may control, for example, a motor configured to extend and/or retract the surgical tool and/or the imaging device. In some embodiments, the surgical tool and the imaging device may be extended or retracted simultaneously. In other embodiments the surgical tool and/or the imaging device may be separately extended or retracted.

The method 900 also comprises extending the imaging device (step 916). The step 904 may be the same as or similar to the step 820 of the method 800 described above as applied to the imaging device. The imaging device may be extended into a borehole formed by the surgical tool in the step 908 above.

The method 900 also comprises receiving an image from the imaging device (step 920). The step 920 may be the same as or similar to the step 804 of the method 800 described above. The image received may depict remaining hard tissue between the borehole formed by the surgical tool in the step 908 and soft tissue.

The method 900 also comprises retracting the imaging device (step 924). The step 924 may be the same as or similar to the step 912 described above as applied to the imaging device.

The method 900 also comprises processing the image (step 928). The step 928 may be the same as or similar to the step 808 of the method 800 described above.

The method 900 also comprises determining a thickness of the hard tissue (step 932). The step 932 may be the same as or similar to the step 812 of the method 800 described above.

The thickness of the hard tissue may be used to determine if the method 900 is to be repeated. If the thickness of the hard tissue meets or exceeds a predetermined threshold, then the method 900 may not be repeated as further drilling may penetrate the hard tissue and damage surrounding soft tissue. If the thickness of the hard tissue does not meet or is less than the predetermined threshold, then the method 900 may be repeated to drill additional material from the hard tissue. The method 900 may be repeated until a desired depth is reached, as indicated by the determined thickness meeting or exceeding the predetermined threshold. Thus, the method 900 reduces a risk of damaging soft tissue when drilling hard tissue by periodically monitoring a thickness of hard tissue being drilled.

It will be appreciated that the steps 916-932 may occur prior to the steps 904-912 in some embodiments. In such embodiments, the steps 916-932 may be executed to determine an initial thickness of the hard tissue. The initial thickness may be used to determine an initial duration of drilling time or an initial depth to drill to.

The present disclosure encompasses embodiments of the method 900 that comprise more or fewer steps than those described above, and/or one or more steps that are different than the steps described above.

FIG. 1000 depicts a method 1000 that may be used, for example, milling and imaging an anatomical element.

The method 1000 (and/or one or more steps thereof) may be carried out or otherwise performed, for example, by at least one processor. The at least one processor may be the same as or similar to the processor(s) 704 of the computing device 702 described above. The at least one processor may be part of a robot (such as a robot 714) or part of a navigation system (such as a navigation system 718). A processor other than any processor described herein may also be used to execute the method 1000. The at least one processor may perform the method 1000 by executing elements stored in a memory such as the memory 706. The elements stored in memory and executed by the processor may cause the processor to execute one or more steps of a function as shown in method 1000. One or more portions of a method 1000 may be performed by the processor executing any of the contents of memory, such as an image processing 720 and/or a segmentation 722.

The method 1000 comprises transmitting instructions to perform a surgical step using a surgical tool (step 1004). The step 1004 may be the same as or similar to the step 816 of the method 800 described above. The surgical tool may be the same as or similar to the surgical tool 108 of a system such as the system 300. The system comprises a housing such as the housing 304 having a bore such as the bore 306. The surgical tool is disposed in the bore. In some embodiments, the surgical tool is a drill bit configured to mill an anatomical element such as the anatomical element 102. The housing also includes an extension such as the extension 302 extending from the housing. The extension may, in some embodiments, comprise a first member such as the first member 308 extending from the housing and a second member such as the second member 314 extending from and perpendicular to the first member. It will be appreciated that in other embodiments, the second member may extend from the first member at any angle.

The system also comprises an imaging device such as the imaging device 312 (which may be the same as or similar to the imaging device 112, 212, 712). In some embodiments, the imaging device may be an ultrasound imaging device. In some embodiments the imaging device is attached to the second member. In other embodiments, the imaging device is integrated with the second member. The imaging device may be used to image an anatomical element comprising soft tissue and hard tissue. During such imaging, the soft tissue and the hard tissue are positioned between the housing and the extension. In other words, the hard tissue and the soft tissue may be positioned between the imaging device and the surgical tool.

The method 1000 also comprises receiving an image depicting hard tissue and soft tissue (step 1008). The step 1008 may be the same as or similar to the step 804 of the method 800 described above.

The method 1000 also comprises processing the image (step 1012). The step 1012 may be the same as or similar to the step 808 of the method 800 described above.

The method 1000 also comprises determining when the soft tissue has separated from the hard tissue (step 1016). Separation of the soft tissue and the hard tissue may be determined by identifying a separation in the hard tissue and the soft tissue identified in the step 1012. In some embodiments, the second member, and thus, the imaging device, may be positioned between the soft tissue and the hard tissue during, for example, surgical procedures such as a laminectomy or a laminotomy. The second member may be used to push the soft tissue and thus, separate the soft tissue from the hard tissue. As such, images obtained from the imaging device during such procedure may typically depict hard tissue and may also sometimes depict soft tissue. More specifically a soft tissue distance between soft tissue and the imaging device (and the second member) may be monitored. When separation occurs, soft tissue may be further from the imaging device and the soft tissue distance may be greater than a soft tissue distance when separation does not occur. For example, the soft tissue distance may be greater than 10 mm when separation occurs and the soft tissue distance may be less than 5 mm when separation does not occur. Thus, if the soft tissue distance is detected in the images as less than 5 mm (for example), then this may indicate that separation between the soft tissue and the hard tissue has not occurred.

In other embodiments, the separation may be determined by identifying a contrast in grayscale or color pixels adjacent to and between the soft tissue and the hard tissue. In other instances, the separation may be determined by a comparison of a first image taken at a first time period and a second image taken at a second time period after the first time period. The separation may be identified by a difference in a spacing of the hard tissue and the soft tissue in the first image as compared to the second image.

It will be appreciated that the steps 1008 to 1016 may occur simultaneously with the step 1004 to monitor the soft tissue and hard tissue separation in real-time or near real-time during the surgical procedure being performed in the step 1004.

The method 1000 also comprises generating a notification (step 1020). The step 1020 may be the same as or similar to the step 824 of the method 800 described above. The notification may be generated when the soft tissue has not separated from the hard tissue (e.g., adhesion barrier may have occurred). When the soft tissue has not separated from the hard tissue, the method 1000 may be paused such that the soft tissue can be separated from the hard tissue using other methods such as, for example, manual separation of the hard tissue and the soft tissue. When the hard tissue and the soft tissue are sufficiently separated, the method 1000 may resume until the surgical procedure is completed.

The method 1000 in use with a system such as the system 300 may be used to mill hard tissue of an anatomical element comprising hard tissue and soft tissue and to image the hard tissue and the soft tissue during a surgical procedure such as a laminectomy or a laminotomy. Images obtained from the imaging device (whether periodically or continuously) may be used to monitor separation of the hard tissue and the soft tissue during the surgical procedure.

The present disclosure encompasses embodiments of the method 1000 that comprise more or fewer steps than those described above, and/or one or more steps that are different than the steps described above.

As noted above, the present disclosure encompasses methods with fewer than all of the steps identified in FIGS. 8, 9, and 10 (and the corresponding description of the methods 800, 900, and 1000), as well as methods that include additional steps beyond those identified in FIGS. 8, 9, and 10 (and the corresponding description of the methods 800, 900, and 1000). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for drilling and imaging an anatomical element, comprising:
  a processor; and
  a memory storing data for processing by the processor, the data, when processed, causes the processor to:
    receive an image from an imaging device coupled to a housing having a bore and a surgical tool disposed in the bore, the image depicting hard tissue;
    process the image using image processing to identify the hard tissue;
    determine a thickness of the hard tissue; and
    control the surgical tool to perform a surgical step on the hard tissue when the thickness is less than a predetermined threshold.

2. The system of claim 1, wherein the imaging device is disposed at an end of the housing and surrounds the bore.

3. The system of claim 1, wherein the imaging device is disposed in the bore and adjacent to the surgical tool.

4. The system of claim 1, the memory stores further data for processing by the processor that, when processed, causes the processor to:
  extend at least one of the surgical tool and the imaging device from the housing.

5. The system of claim 1, wherein the surgical tool comprises a drill bit and the surgical step comprises drilling the anatomical element.

6. The system of claim 1, wherein the memory stores further data for processing by the processor that, when processed, causes the processor to:
  generate a notification when the thickness of the hard tissue meets a target thickness.

7. The system of claim 1, wherein the memory stores further data for processing by the processor that, when processed, causes the processor to:
  prevent the surgical tool from further advancement when the thickness of the hard tissue meets a target thickness.

8. The system of claim 1, wherein the imaging device comprises an ultrasound device.

9. A system for drilling and imaging an anatomical element, comprising:
  a housing comprising a bore;
  a surgical tool disposed in the bore, the surgical tool operable to extend from the bore and perform a surgical step;
  an imaging device disposed in the bore and adjacent to a drill bit of the surgical tool, the imaging device operable to extend from the bore and obtain an image;
  a processor; and
  a memory storing data for processing by the processor, the data, when processed, causes the processor to:
    control the surgical tool to perform the surgical step;
    receive the image from the imaging device depicting hard tissue;
    process the image using image processing to identify the hard tissue; and
    determine a thickness of the hard tissue.

10. The system of claim 9, wherein the memory stores further data for processing by the processor that, when processed, causes the processor to:
  generate a notification when the thickness of the hard tissue meets or exceeds a thickness threshold.

11. The system of claim 9, wherein the surgical step comprises drilling the anatomical element.

12. The system of claim 9, wherein the system further comprises:
  an irrigation source operable to provide liquid to the bore; and
  a vacuum source operable to remove the liquid from the bore.

13. The system of claim 9, wherein when the thickness of the hard tissue is less than a thickness threshold, and wherein the memory stores further data for processing by the processor that, when processed, causes the processor to:
  extend the surgical tool from the bore; and
  retract the surgical tool into the bore.

14. A system for milling and imaging an anatomical element, comprising:
  a housing having a bore and an extension extending from the housing;
  a surgical tool disposed in the bore, the surgical tool operable to extend from the bore and perform a surgical step;
  an imaging device disposed at an end of the extension and opposite the surgical tool;
  a processor; and
  a memory storing data for processing by the processor, the data, when processed, causing the processor to:
    control the surgical tool to perform the surgical step;
    receive an image from the imaging device depicting hard tissue and soft tissue;
    process the image using image processing to identify the hard tissue and the soft tissue; and
    determine when the soft tissue has separated from the hard tissue.

15. The system of claim 14, wherein the soft tissue and the hard tissue is positioned between the surgical tool and the imaging device.

16. The system of claim 14, wherein the memory stores further data for processing by the processor that, when processed, causes the processor to:
  generate a notification when the soft tissue does not separate from the hard tissue.

17. The system of claim 14, wherein the surgical tool comprises a drill bit and the surgical step comprises milling an anatomical element.

18. The system of claim 14, wherein the extension comprises a first member extending from the housing and a second member extending from and perpendicular to the first member.

19. The system of claim 18, wherein the imaging device is at least one of attached to or integrated with the second member.

* * * * *